United States Patent
Nempont et al.

(10) Patent No.: US 10,410,347 B2
(45) Date of Patent: Sep. 10, 2019

(54) DIGITAL SUBTRACTION ANGIOGRAPHY (71) Applicant: KONINKLIJKE PHILIPS N.V., Eindhoven (NL)

(72) Inventors: Olivier Pierre Nempont, Suresnes (FR); Guilaume Julien Joseph Pizaine, Issy-les-Moulineaux (FR); Raoul Florent, Ville d'Avray (FR); Vincent Maurice André Auvray, Meudon (FR)

(73) Assignee: KONINKLIJKE PHILIPS N.V., Eindhoven (NL)

(*) Notice: Subject to any disclaimer, the term of this patent is extended or adjusted under 35 U.S.C. 154(b) by 100 days.

(21) Appl. No.: 15/529,397

(22) PCT Filed: Oct. 29, 2015

(86) PCT No.: PCT/EP2015/075131
§ 371 (c)(1),
(2) Date: May 24, 2017

(87) PCT Pub. No.: WO2016/083068
PCT Pub. Date: Jun. 2, 2016

(65) Prior Publication Data
US 2017/0262989 A1    Sep. 14, 2017

(30) Foreign Application Priority Data
Nov. 25, 2014  (EP) .................... 14306877

(51) Int. Cl.
*A61B 6/00*  (2006.01)
*G06T 7/00*  (2017.01)
(Continued)

(52) U.S. Cl.
CPC ............ *G06T 7/0016* (2013.01); *A61B 6/461* (2013.01); *A61B 6/504* (2013.01); *A61B 6/5205* (2013.01);
(Continued)

(58) Field of Classification Search
CPC ................ A61B 5/00; A61B 6/00; G06T 7/00
(Continued)

(56) References Cited

U.S. PATENT DOCUMENTS 4,729,379 A * 3/1988 Ohe .................. A61B 6/481
348/E5.089

FOREIGN PATENT DOCUMENTS

| EP | 1542165 A1 | 6/2005 |
|---|---|---|
| JP | 201430506 A | 2/2014 |
| WO | 2011110987 A1 | 9/2011 |

OTHER PUBLICATIONS

Auvray, Vincent ET AL "Multiresolution Parametric Estimation of Transparent Motions and Denoising of Fluoroscopic Images", Medical Image Computing and Computer-Assisted Intervention—MICCAI 2005.

* cited by examiner

Primary Examiner — Abolfazl Tabatabai (57) ABSTRACT (DSA) enables the vascular structure around a heart to be displayed using the injection of a contrast medium while the heart is being observed by an X-ray apparatus. The quality of a DSA sequence can be affected by the breathing of the patient, when under examination. This is because the images forming a DSA sequence are gathered using an X-ray modality, and therefore the independent movement of transparent tissues inside a patient causes motion artifacts to appear in DSA images. According to an aspect of the present invention, a method, device, X-ray system, computer program element, and a computer readable medium are provided which can correct artifacts appearing in DSA images which originate from to the motion of the heart and the motion caused by breathing in a patient.

14 Claims, 5 Drawing Sheets

(51) Int. Cl.
*G06T 5/50* (2006.01)
*G06T 7/20* (2017.01)
*A61K 9/00* (2006.01)

(52) U.S. Cl.
CPC .......... *A61B 6/5235* (2013.01); *A61B 6/5264* (2013.01); *A61B 6/5288* (2013.01); *G06T 5/50* (2013.01); *G06T 7/20* (2013.01); *G06T 2207/10116* (2013.01)

(58) Field of Classification Search
USPC ....................................................... 382/132
See application file for complete search history.

DIGITAL SUBTRACTION ANGIOGRAPHY

CROSS-REFERENCE TO PRIOR APPLICATIONS

This application is the U.S. National Phase application under 35 U.S.C. § 371 of International Application No. PCT/EP2015/075131, filed on Oct. 29, 2015, which claims the benefit of European Patent Application No. 14306877.3, filed on Nov. 25, 2014. These applications are hereby incorporated by reference herein.

FIELD OF THE INVENTION

The present invention relates to a device for providing a digital subtraction angiogram, a method for providing a digital subtraction angiogram, an X-ray imaging arrangement, a computer program element, and a computer-readable medium.

BACKGROUND OF THE INVENTION

Digital subtraction angiography (DSA) is an X-ray imaging method which removes background structures from the final image. A mask image containing the background structures is acquired. Subsequently, contrast medium is injected. An image is then acquired of blood vessels and of perfused tissues containing the contrast medium. The mask image is subtracted from the image containing the injected blood vessels and perfused tissues. In this way, there is improved contrast between blood vessels or tissues, and their background.

U.S. Pat. No. 4,729,379 discusses digital subtraction angiography. Unfortunately, the DSA technique is less useful in cardiac procedures, because it is sensitive to patient motion.

SUMMARY OF THE INVENTION

It would be advantageous to have an improved technique for providing cardiac digital subtraction angiography.

The object of the present invention is solved by the subject-matter of the independent claims, wherein further embodiments are incorporated in the dependent claims. It should be noted that the following described aspects of the invention apply also for the device for providing a digital subtraction angiogram, the method for providing a robust digital subtraction angiogram and to the X-ray imaging arrangement, as well to the computer program element and the computer readable medium.

Towards this end, a first aspect of the invention provides a device for providing a digital subtraction angiogram, comprising
an interface unit;
a processing unit; and
an output unit.

The interface unit is configured to provide (i) a cardiac phase image sequence comprising a plurality of cardiac phase images, (ii) a breathing phase image sequence comprising a plurality of breathing phase images, and (iii) an intervention image, wherein the intervention image is indexed with a first cardiac phase index.

The processing unit is configured to select a first breathing phase image in the plurality of breathing phase images which is at a similar breathing phase to the intervention image, wherein the first breathing phase image is indexed with a second cardiac phase index, and to generate a breathing corrected intervention image by subtracting the first breathing phase image from the intervention image, and to select a first cardiac phase image corresponding to the second cardiac phase index, and to select a second cardiac phase image corresponding to the first cardiac phase index, and to generate a cardiac phase corrected image by subtracting the first cardiac phase image from the second cardiac phase image, and to compensate the cardiac phase corrected image to account for breathing motions, and to subtract the motion compensated cardiac phase corrected image from the breathing corrected intervention image.

The output unit is configured to display the angiogram image to a user.

Advantageously, a device for providing a digital subtraction angiogram according to the first aspect compensates for the contrary motion of overlying tissue layers in a digital subtraction angiogram, which appear owing to the X-ray transparency of the tissue layers.

Additionally, a patient undergoing such an examination does not need to hold his or her breath for a long time, because only one heart cycle needs to be captured, at a stable breathing status. Typically, a device according to the first aspect of the invention requires the patient to hold his or her breath for only one second, versus the usual requirement for a patient to hold his or her breath for between ten to twenty seconds in the existing protocols.

Additionally, a device for providing a digital subtraction angiogram in accordance with the first aspect of the invention increases the visibility of a patient's blood vessels and perfused tissues, because the blurring and artefacts connected with patient motion, in particular with the patient's breathing, are removed. This allows a reduction in the amount of contrast agent injected into the patient.

Additionally, a device according to a first aspect of the invention allows cardiac perfusion examinations to emerge with fewer visual artefacts. Perfusion examinations last much longer than classical angiography examinations, and so the effect of residual motion caused, for example, by patient breathing, is worsened in a perfusion examination.

According to a second aspect of the invention, a method for providing a robust digital subtraction angiogram is provided. The method comprises the following steps:

a) providing (i) a cardiac phase image sequence comprising a plurality of cardiac phase images, (ii) a breathing phase image sequence comprising a plurality of breathing phase images, and (iii) an intervention image, wherein the intervention image is indexed with a first cardiac phase index;

b) selecting a first breathing phase image in the plurality of breathing phase images which is at a similar breathing phase to the intervention image, wherein the first breathing phase image is indexed with a second cardiac phase index;

c) generating a breathing corrected intervention image by subtracting the first breathing phase image from the intervention image;

d) selecting a first cardiac phase image corresponding to the second cardiac phase index;

e) selecting a second cardiac phase image corresponding to the first cardiac phase index;

f) generating a cardiac phase corrected image by subtracting the first cardiac phase image from the second cardiac phase image;

g) motion compensating the cardiac phase corrected image to account for breathing motions;

h) subtracting the motion compensated cardiac phase corrected image from the breathing corrected intervention image to provide an angiogram image; and i) displaying the angiogram image.

The use of a method according to the second aspect of the invention results in the advantages discussed above in connection with the first aspect.

According to a third aspect of the invention, an X-ray imaging arrangement is provided. The X-ray imaging arrangement comprises:

an X-ray acquisition device with an X-ray source and an X-ray detector; and a device for providing a digital subtraction angiogram as previously described.

The X-ray image acquisition device is configured to acquire image data of the chest of a patient and provide the data to the interface of the device for providing a digital subtraction angiogram.

Advantageously, the use of an X-ray imaging arrangement according to the third aspect of the invention results in the advantages discussed above in connection with the first aspect.

According to a fourth aspect of the invention, there is provided a computer program element for controlling an apparatus as previously describes which, when the computer program element is executed by a processing unit, is adapted to perform the method steps as previously described.

Advantageously, the use of a computer program element according to the fourth aspect of the invention results in the advantages discussed above in connection with the first aspect.

According to a fifth aspect of the invention, there is provided a computer-readable medium having stored the program element as previously described.

Advantageously, the use of a computer program element according to the fifth aspect of the invention results in the advantages discussed above in connection with the first aspect.

The term "a cardiac phase image sequence", "a breathing phase image sequence", and "an intervention image" should be understood to refer to sequences of images that originate from an X-ray image sequence. The cardiac phase image sequence is, preferably, acquired under breath-hold, and contains at least one heart cycle. Typically, it will be as short as one second. The breathing phase image sequence is typically longer than the cardiac phase image sequence, and contains at least one half of a breathing cycle, acquired from the fully exhaled to fully inhaled state. For example, the breathing cycle may extend from exhalation to inhalation, or vice versa. During the acquisition of the cardiac phase image sequence and the breathing phase image sequence, contrast agent is not present. The intervention image is diagnostic image obtained following injection of the contrast medium, at which point the patient is free to breathe normally. An intervention image is an image captured after the contrast medium has been injected into the patient.

The term "indexed with a (first or second) cardiac phase index" as applied in this specification refers to the fact that the instant of capture of a cardiac image in the cardiac phase image sequence can be temporally related to a certain heart phase by assigning indices to each image in the cardiac phase image sequence. The indices can be integers relating to the frame number of a cardiac phase image sequence, or absolute time-stamps, or a measure derived from an electrocardiogram (ECG). Alternatively, because a heart cycle is a repetitive process, the index may be an angle measured in degrees or radians. Many different types of indexing will be applicable, provided they allow the synchronization of the intervention image to the cardiac cycle of the patient. As an alternative, the cardiac phase index could be determined using an image processing operation on the cardiac phase image sequence.

The term "breathing phase" denotes a one of many possible transition states of the thorax in-between a state of maximum exhalation (0%) and maximum inhalation (100%), or vice-versa. The breathing phase can be denoted by a percentage, or (because it is cyclic) an angle in degrees or radians. Alternatively, it may be defined with reference to a breathing phase image index applied to the images of the breathing phase image sequence. Many techniques to derive the breathing phase could be applied. For example, the deflection of the diaphragm could be tracked between extreme points, using a segmentation approach.

Therefore, it may be considered as a further aspect of the invention that a double-subtraction scheme is provided. The first subtraction subtracts background, and breathing-related structures. The second subtraction removes residual cardiac motion artefacts.

These and other aspects of the present invention will become apparent from and be elucidated with reference to the embodiments described hereinafter.

BRIEF DESCRIPTION OF THE DRAWINGS

Exemplary embodiments of the invention will be described with reference to the following drawings.

DETAILED DESCRIPTION OF EMBODIMENTS

X-ray imaging can be used to study cardiac problems, such as stenosis in coronary arteries. During this procedure, a contrast agent is injected into the cardiac vasculature via a catheter. Simultaneously, X-ray equipment records an angiographic sequence of the cardiac region as the contrast medium propagates in the vasculature. Such diagnostic angiograms permit diagnosis and intervention of coronary stenosis.

Furthermore, myocardial perfusion can be studied. It is difficult to study myocardial perfusion from the shape of the vasculature alone, as would be obtained in a standard X-ray imaging procedure. There is no one-to-one relation between the appearance of the coronary vasculature, and myocardial perfusion.

In particular, the study of myocardial perfusion requires relatively long X-ray procedures. Whereas to study coronary stenosis, an exposure of between three and five seconds would be sufficient (the exact amount depends on the contrast agent inflow rate), a perfusion study could last between fifteen and twenty seconds. Over a time period of one second, substantially the only structure moving in the thorax is the heart. Over fifteen to twenty seconds, there will be several breath motions in the thorax, which cause a residual motion between mask frames and the intervention image. This effect is a particular problem with elderly patients, who can usually only hold his or her breath for up to five seconds. Neither conventional DSA, nor conventional cardiac DSA can accurately correct for the breath motion.

Therefore, residual motion can result in visible artefacts in a DSA image, thus reducing the quality of the images to the extent that they become diagnostically useless.

A possible solution is for a patient to hold his or her breath for a long time during an examination. Perfusion examinations can last up to twenty seconds, and so it can be difficult to cancel residual motions simply by asking the patient to hold his or her breath.

Figure 1:
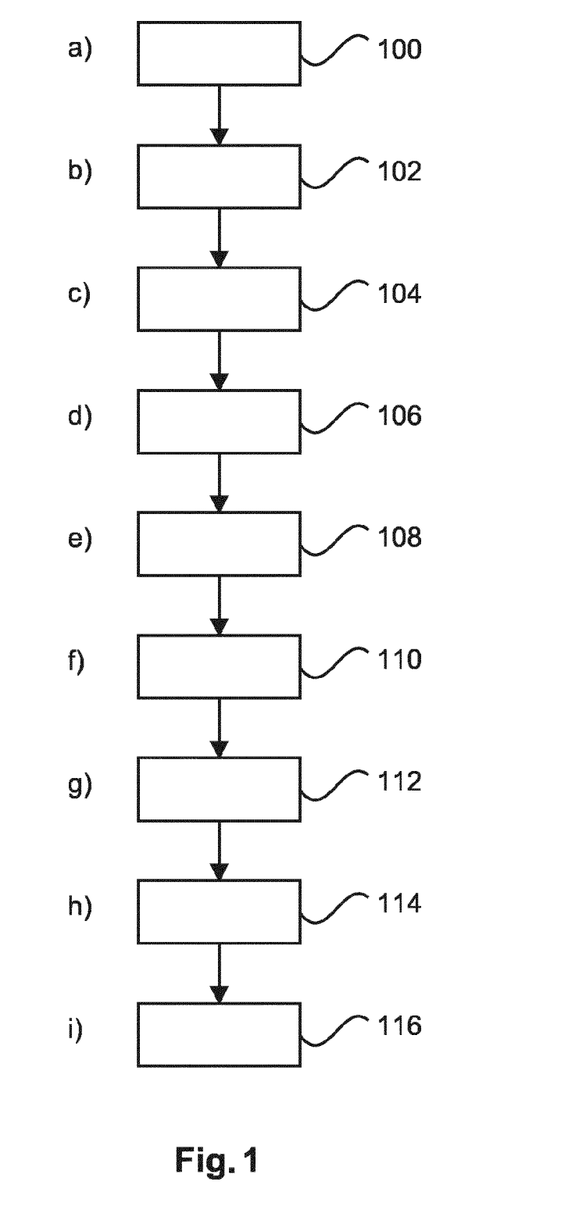
FIG. 1 shows a method according to an aspect of the invention.

According to an aspect of the invention, a method for providing a robust digital subtraction angiogram is provided. The method comprises the following steps:

a) providing 100 (i) a cardiac phase image sequence comprising a plurality of cardiac phase images, (ii) a breathing phase image sequence comprising a plurality of breathing phase images, and (iii) an intervention image, wherein the intervention image is indexed with a first cardiac phase index;

b) selecting 102 a first breathing phase image in the plurality of breathing phase images which is at a similar breathing phase to the intervention image, wherein the first breathing phase image is indexed with a second cardiac phase index;

c) generating 104 a breathing corrected intervention image by subtracting the first breathing phase image from the intervention image;

d) selecting 106 a first cardiac phase image corresponding to the second cardiac phase index;

e) selecting 108 a second cardiac phase image corresponding to the first cardiac phase index;

f) generating 110 a cardiac phase corrected image by subtracting the first cardiac phase image from the second cardiac phase image;

g) motion compensating 112 the cardiac phase corrected image to account for breathing motions;

h) subtracting 114 the motion compensated cardiac phase corrected image from the breathing corrected intervention image to provide an angiogram image;

i) displaying 116 the angiogram image.

An algorithm according to the method discussed above performs two consecutive subtractions. The first subtraction, in step c) 104, removes the static background and the tissues animated by breathing motion. The second subtraction, in step d) 106, removes tissues animated by cardiac motion, which includes the cardiac muscle and associated blood vessels and tissue surrounding the heart.

An injected muscle will appear so that areas of tissue absorbing X-rays in the conventional way are removed from the image the so-called "regular tissue absorption". The additional contrast agent contained in the tissue will remain in the image, and will be distinctly visible over the flat background, after the subtraction.

A method according to this aspect of the invention is illustrated in FIG. 1, and will now be further explained.

Initially, a sequence of images is acquired from a patient. Typically, the sequence will be acquired as a sequence of angiogram images before and during an injection of contrast agent.

A typical operational protocol comprises obtaining a short X-ray sequence $S_a$ acquired under conditions where the patient holds his or her breath. The sequence $S_a$ contains at least one heart cycle. The length of the sequence $S_a$ could typically could be as short as one second.

A longer sequence $S_b$, which contains one half of a breathing cycle, covering the entire breathing amplitude from fully exhaled, to fully inhaled, is also obtained. In other words, a sequence of angiogram images containing one half cycle from exhalation to inhalation, or from inhalation to exhalation, is obtained.

According to an embodiment of the invention, the sequence $S_b$ may be obtained before the sequence $S_a$.

Then, a clinician injects a contrast agent. Images obtained during the contrast injection phase are referred to as intervention images I. The intervention image is associated with a first cardiac phase index. During a typical application of this protocol, a sequence of angiogram images is obtained in rapid succession containing the cardiac phase image sequence, the breathing phase image sequence, and an intervention image.

In the following, a cardiac phase image sequence is denoted using the reference $S_a$. A breathing phase image sequence is denoted $S_b$. An intervention image is denoted I. These individual sections of the input angiogram sequence may be identified in the input image sequence (X-ray image sequence) automatically, by image processing techniques, or by user input, and the sequences may be automatically provided.

When the cardiac phase image sequence $S_a$, the breathing phase image sequence $S_b$, and the intervention image I have been parsed for use, processing can begin.

The overall architecture of the algorithm is firstly to remove the static background and the tissues animated by the breathing motion only, and then to subtract the artefacts caused by the tissues being animated by the cardiac motion. Therefore, step b) 102 selects a first breathing phase image in the breathing phase image sequence $S_b$, which is at a similar breathing status to the breathing status present in the intervention image I.

The first breathing phase image is indexed with a second cardiac phase index. In other words, a given breathing phase image will be obtained when the heart is at a specific status, and this specific heart status is present in the sequence $S_a$, because the sequence $S_a$ is captured over a complete cycle. As will be discussed below, the cardiac phase index may be provided externally, or derived via image processing.

In an example, an image processing algorithm is provided which identifies the breathing status of the thorax (for instance by following the diaphragm position), shown in the intervention image I. The breathing phase image sequence is then searched to find an image with a breathing status which is most similar to that of the intervention image.

Of course, other methods of finding a frame with a similar breathing status to the intervention image could be used.

The breathing phase frame identified in this way is denoted as mask image $M_b$. The mask image $M_b$ is subtracted from the intervention image I. This results in difference image $D_1$. In difference image $D_1$, the static background tissues, and the tissues animated by the movement indexed with breathing, are removed. This is because they have a close spatial relationship in intervention image I, and mask image $M_b$.

It will be noted that tissue affected by cardiac movement in intervention image I and mask image $M_b$ will remain as an artefact in the difference image $D_1$. This is because there is no requirement on the cardiac phase in intervention image I and mask image $M_b$. In other words, the difference image $D_1$ contains the difference of the cardiac tissues at the two heart phases of intervention image I and mask image $M_b$.

For convenience, the cardiac phase during an acquisition of the intervention image I is denoted $s_I$. The cardiac phase during the acquisition of the mask image $M_b$ is denoted $s_{MB}$. Having in step c) 104 performed the first subtraction $D_1$, which has the effect of removing the residual breathing motion, the algorithm then subtracts the tissues animated only by cardiac motion.

In the selection step d) 106, a search in sequence $S_a$ is performed (the full cycle of cardiac motion) for an image containing the heart at a heart phase $s_I$. In the selection step e) 108 a search in sequence $S_a$ is performed for an image of the heart at a heart phase $s_{MB}$.

The process of searching for the mask image $M_b$ in the sequence $S_b$, and the process of selecting the two cardiac images in $S_a$ at different heart phases $s_I$ and $s_{MB}$ is an heuristic search process, which could be achieved in many different ways.

According to one example, an implicit search procedure could be used. The image of the heart in the intervention image I could be treated using a well-known in the art "water-filling" algorithm to highlight areas of the frame occupied by cardiac tissue. A similar water-filling algorithm could be applied to individual cardiac images in the sequence $S_a$. Then, the frame in the sequence $S_a$ which had the most similar water-filling algorithm result to that of the intervention frame I would be identified as the frame in the sequence $S_a$ containing a cardiac image at a similar heart phase.

Alternatively, the state of the heart or the diaphragm position could be estimated explicitly by identifying important dimensions, contours, or structures, such as the external boundary of the heart, or the deflection of the diaphragm in the thorax. Then, the cardiac or breathing status could be estimated explicitly, and compared to the intervention image.

Alternatively, the cardiac status and the breathing status can be physically measured at the time of recording the X-ray image sequence. External breathing phase information can be provided by an electronic chest band which measures the breathing status by monitoring the circumference of the thorax. Cardiac status may be measured by an electrocardiogram (ECG), as is known. These physical measurements are temporally indexed to the X-ray image sequence, so that the intervention image I can be explicitly referenced to frames in the sequences $S_a$ and $S_b$.

Therefore, in steps d) 106 and e) 108, cardiac phase images sharing, respectively, the heart phase ($s_I$) of the intervention image (the second cardiac phase index), and the heart phase ($s_{MB}$) of the breathing mask image (the first cardiac phase index) are identified in the sequence $S_a$. Then, the difference image $D_M$ between these two images is found, by subtracting one image from the other. In the difference image $D_M$, the static background and respiratory tissues that are static in the sequence $S_a$ disappear. The result of this second subtraction is a difference image where only the difference of the heart position at phases $s_I$ and $s_{MB}$ is visible.

Typically, the difference image $D_M$ is compensated using motion compensation. The motion compensation is intended to compensate for a global difference in the position of the heart in the patient's chest due to their breathing. Such compensations are known in the art, ranging from global translation, or globally affine, to the estimation of dense velocity fields. This motion compensation uses information from first subtraction image $D_1$ to enhance the estimation of the heart's movement.

The final phase of the method is to subtract the motion-compensated difference image $D_M$ from difference image $D_1$, which causes the difference owing to cardiac motion between phases $s_I$ and $s_{MB}$ to disappear.

Thus, a method has been described which allows the derivation of images containing overlaid transparent tissues which are animations by a long-term repetitive motion, such as a breathing motion, and a shorter repetitive motion, such as a cardiac motion.

This method can remove the large amplitude motions in a DSA image which are mixed together, owing to the tissue transparency. In addition, there is no reason for a patient to hold his or her breath for the length of an entire perfusion examination.

Figure 2:
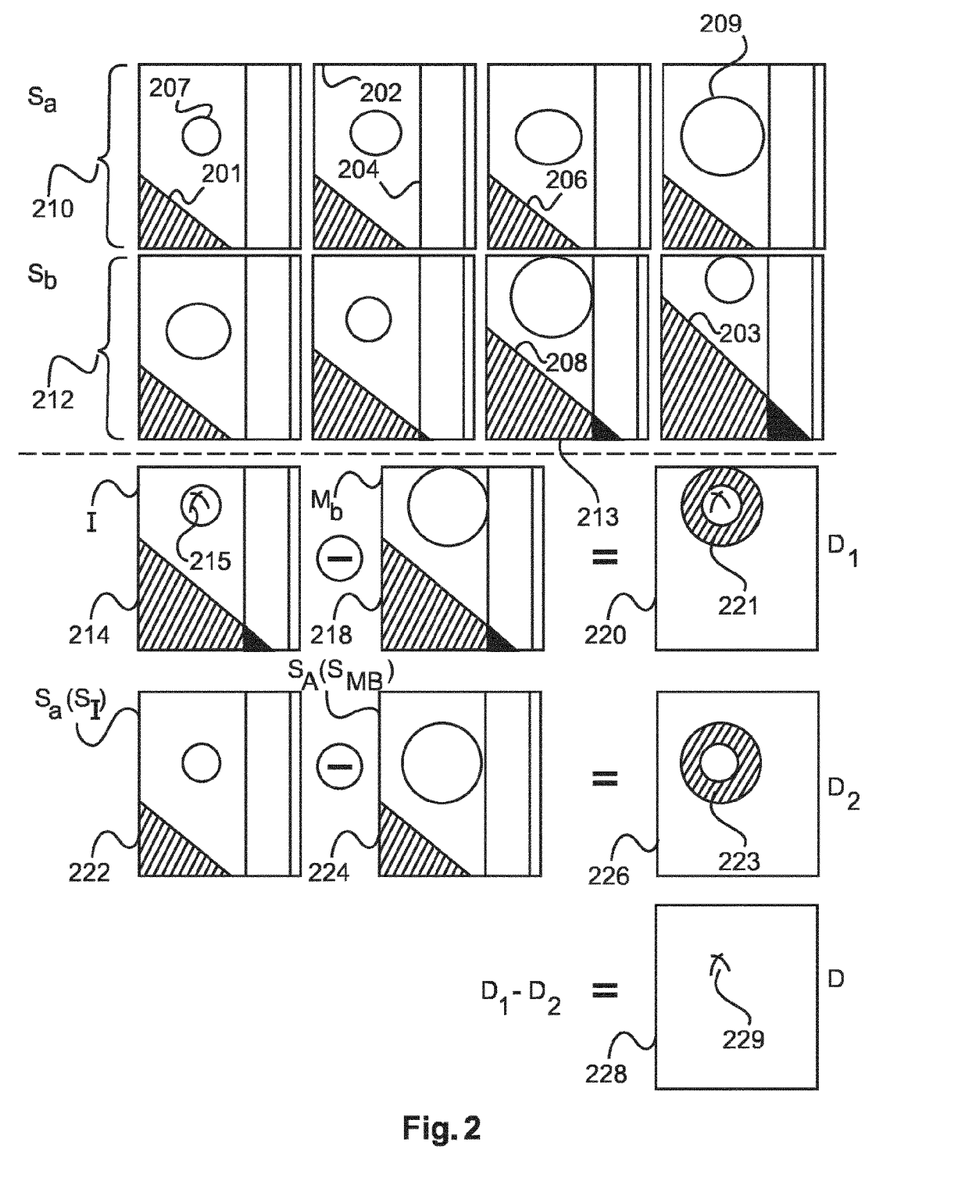
FIG. 2 illustrates the operation of the method.

FIG. 2 provides a graphical representation of the functioning of the algorithm previously described. The cardiac phase image sequence $S_a$ is illustrated in sequence 210, and the breathing phase image sequence $S_b$ is illustrated in sequence 212. The rectangular frames are illustrated in a schematic sense to show the independence of the cardiac and the breathing motions. In connection with this, the schematic representation is now explained.

For each rectangular frame 202 representing, in this example, the thoracic area of a patient, feature 204 represents a permanently static feature, such as the spinal column 204. The spinal column will remain static during a typical DSA examination, although it will be appreciated that if the patient moves unpredictably, or if the clinician horizontally translates the table, then the spinal column will move.

The diaphragm 206 is represented in the frames using a diagonal line. The extent of the diagonal line across the rectangle 202 represents the breathing status in each frame. Therefore, in sequence $S_a$, the diaphragm 201 illustrates an exhaled state, and diaphragm 203 in sequence $S_b$ illustrates an inhaled state. The heart is represented by the circle 207 at its smallest extent (systole), and the circle 209 at its largest extent (diastole) in sequence $S_a$ 210.

The operation of the method using this notation will now be described.

Initially, the patient is asked to hold his or her breath while the cardiac phase image sequence $S_a$ 210 is obtained. Then, the patient is requested to breathe so that the breathing phase image sequence $S_b$ is acquired 212. Finally, contrast agent is injected and the intervention frame I 214 is obtained. It will be appreciated that the intervention frame may be part of a sequence of intervention frames, although in its simplest form the method can be applied to one intervention frame. The intervention frame 214 contains a heart with its coronary arteries visible as black lines, denoting an injection of contrast agent. The perfusion is visible in the shaded area around the black lines.

The breathing phase image sequence is searched for a first breathing phase image 213 containing an anatomical feature, having a similar or the same status to the same anatomical feature in frame 214, also denoted as I. In an example, this may be detected via diaphragm position 208. This frame is designated as the mask image $M_b$.

The subtraction (step c) 104 subtracts the mask image $M_b$ from the intervention image I. This yields difference image 220, also denoted as $D_1$. As can be seen by the blank thoracic region, frame 220 does not have the static artefact of the spine 204 and the artefact of the diaphragm 208. Because this frame is not referenced to any cardiac motion, a ghosted area 221 appears around the heart, representing the different arrangement of the heart, and its surrounding tissues, at different images of the breathing phase image sequence. Thus, a breathing corrected intervention image has been generated.

The next phase of the method (step d) 106 involves searching for a first cardiac phase image at the same cardiac phase $s_I$ (the second cardiac phase index) as the intervention image in $S_a$. This first cardiac phase image is represented by frame 222.

A second search operation (step e) 108 takes place to find the cardiac image which represents the cardiac phase $s_{MB}$ (the first cardiac phase index) at the instant of capturing the breathing phase image used as the mask image 218, also denoted as $M_B$. This is represented by frame 224.

The subtraction of these frames (at step f) 110 is the second subtraction in the double subtraction algorithm method, and results in image 226, also denoted as $D_2$. In image $D_2$, the static background, and the respiratory tissues have disappeared, yielding a difference image 226 where only the difference of the heart at phases $s_I$ and $s_{MB}$ is visible. The difference is denoted by the area 223 in FIG. 2.

The motion compensation step, which is a global compensation step compensating for the movement of the entire heart caused by the breathing motion, is not shown in FIG. 2. The result of subtracting $D_1$ from $D_2$ yields final output frame 228, also denoted as D, which only contains regions of the original intervention frame I containing contrast agent 229. Although in FIG. 2 the contrast agent is shown as the traces of arteries, it will be appreciated that after a long perfusion examination lasting up to 20 seconds, the contrast agent will have dissipated into the surrounding tissue, appearing as areas of brighter or darker myocardial tissue, allowing a more reliable perfusion examination.

Figure 3:
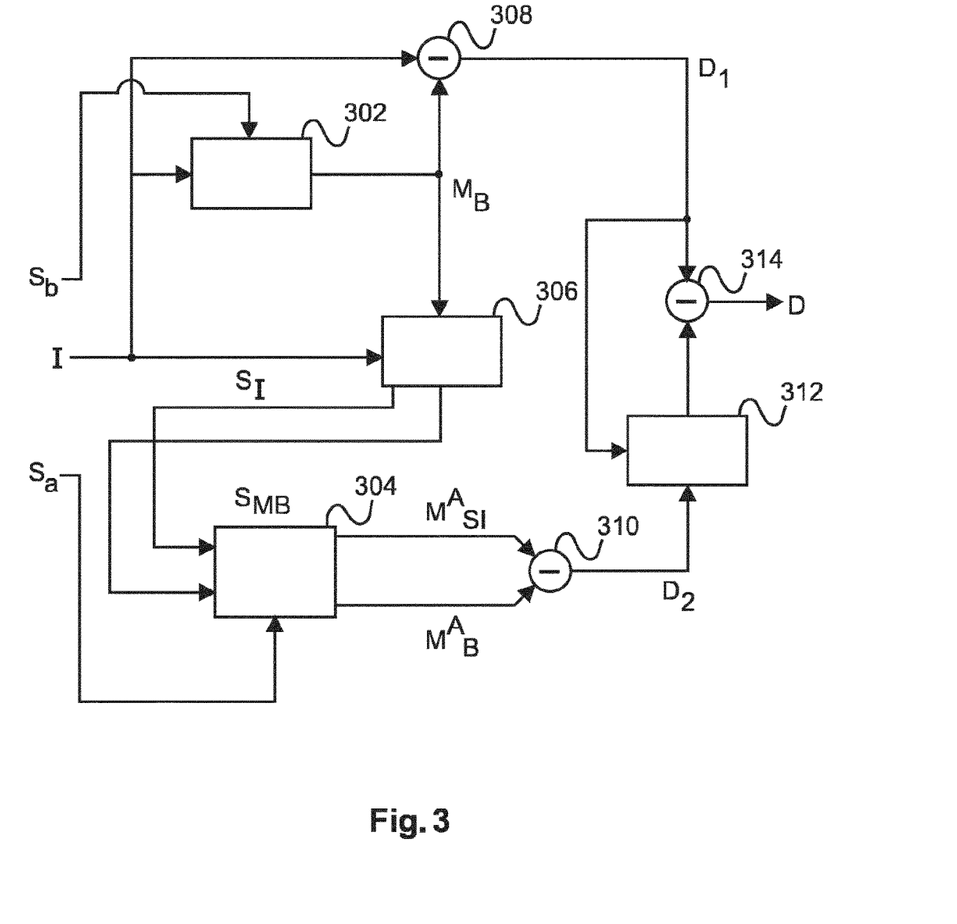
FIG. 3 is a system diagram of an image processing process.

FIG. 3 is a schematic block diagram of a system which can perform the aforementioned method. It will be appreciated that the system can be implemented as software running on a computer system, on a microprocessor or on a digital signal processor, or using specific hardware, such as a field-programmable gate array, or custom hardware, or any combination of these methods.

The processing stages outlined herein may be performed in any order, provided that the data dependencies inferred herein are respected.

The algorithm takes as inputs a cardiac phase image sequence $S_a$, an intervention image I, and a breathing phase image sequence $S_b$.

The intervention image I and the breathing phase image sequence $S_b$ are input into a first breathing phase image selector 302, which provides the mask image $M_b$.

Subtractor 308 provides the subtraction image $D_1$. The intervention image I and the first breathing phase image $M_b$ are input into a heart phase identification module 306, which searches for the heart phase of the first breathing phase image $M_b$ (indexed to a second cardiac phase index $s_{MB}$) and the cardiac phase index of the intervention image $S_I$ (the first cardiac phase index).

The first cardiac phase index and the second cardiac phase index are input into cardiac mask phase selector 304. The output of this block is the mask image $M^A_{SI}$, and cardiac mask image $M^A_B$, which are then subtracted 310 from each other to yield $D_2$.

$D_2$ is input into motion-compensation module 312 to compensate for motion of the heart owing to a large-scale motion, such as a breathing action, which uses a reference to D1 to compute the motion of the heart from D1 to D2.

The motion-compensated image $D_2$ and the subtraction image $D_1$ are input into subtractor 314 to yield the output image D.

According to an embodiment of the invention, a method is provided as previously discussed, wherein step a) further comprises:

a1) providing external breathing phase information, wherein the breathing phase image sequence and the intervention image are synchronized to the external breathing phase information; and wherein step b) further comprises:

b1) comparing the external breathing phase information indexed with the intervention image to the external breathing phase information indexed with the images of the breathing phase image sequence;

b2) identifying the first breathing phase image as the image in the breathing phase image sequence which is at a similar breathing phase to the intervention image.

According to this embodiment, the first breathing phase image may be identified using external breathing phase information. This may be provided using a chest band, which tracks the expansion and contraction of the patient's thorax as he or she breathes. As the X-ray images are captured from the patient, they are each indexed to a relative dilation of the chest band, and thus indexed to a specific breathing status. In this way, breathing phase images are indexed and searched for without using image processing.

According to an embodiment of the invention, a method is provided, wherein step b) further comprises:

b3) comparing the intervention image to each breathing phase image in the breathing phase image sequence to derive a first series of match metrics;

b4) selecting as the first breathing phase image the breathing phase image in the breathing phase image sequence which has the best match metric of the first series of match metrics.

According to this embodiment, each breathing phase image in the breathing phase image sequence has an image processing algorithm applied to it which summarizes the breathing status of the image in a series of match metrics. The match metrics may be compared with a similar match metric of the intervention image to identify the first breathing phase image.

According to an embodiment of the invention, the match metric is derived using a water-filling algorithm.

According to an embodiment of the invention, the match metric is derived using the square root of squared differences, or the entropy, or the mutual information.

According to an embodiment of the invention, small residual motions are corrected using deformation corrections by block matching, potentially with vessel masking.

According to an embodiment of the invention, the method is provided as described previously, wherein step b) further comprises:

b5) estimating the breathing status of each image in the breathing phase image sequence;

b6) estimating the breathing status of the intervention image;

b7) selecting as a first breathing phase image the breathing phase image in the breathing phase image sequence which has the closest breathing status to the breathing status of the intervention image.

Therefore, in this embodiment, a breathing status of the patient is explicitly determined, and is used to determine the first breathing phase image.

In an example of an explicit method of determining the breathing status, a breathing phase image is segmented. Then, a typical structure such as the diaphragm is identified in the image, by calculating a figure-of-merit characterizing the structure, for example a deflection spline fitted to the diaphragm. A comparison between the diaphragm's deflection spline with other deflection splines in the sequence of breathing phase images is made. The most similar spline identifies the breathing phase image which is most similar to the intervention image.

Alternatively, an explicit segmentation of the rib position could be applied.

According to an embodiment of the invention, the breathing status may be derived by tracking the status of the barycentre of the grey levels in the image of the thorax.

According to an embodiment of the invention, the breathing status may be derived by tracking the status of the projection along the spine of the barycentre of the grey levels.

Any other metric gathering the global vertical motion (ie, along the spine of the patient) could be exploited. For example, one could perform a motion estimation by block matching identical features in successive images, compared to to a reference image of the sequence. The median value of the estimated motions of the blocks would provide a a breathing metric for each considered frame.

According to an embodiment of the invention, a method is provided as described previously, wherein step a) further comprises:

a2) providing external cardiac phase information synchronized to the cardiac phase image sequence; and wherein step c) further comprises:

d1) selecting the first cardiac phase image corresponding to the second cardiac phase index using the external cardiac phase information;

and/or wherein step e) further comprises:

e1) selecting the second cardiac phase image corresponding to the first cardiac phase index using the external cardiac phase information.

Therefore, the cardiac phase image sequence may be synchronized to an external source defining the cardiac status. In this case, image processing is not required for synchronization of the cardiac status to the image sequences, because the match between the intervention image frame to the cardiac phase image sequence is achieved using the external cardiac phase information.

According to an embodiment of the invention, the external cardiac phase information is provided using an echocardiogram (ECG). The use of an ECG signal could be used to more easily provide information about the cardiac status of the patient, and to synchronize the cardiac phase and breathing phase frames.

According to an embodiment of the invention, a method is provided according to the method described previously, wherein step d) further comprises:

d2) comparing the intervention image to each cardiac phase image in the cardiac phase image sequence to derive a second series of match metrics;

d3) selecting as the second cardiac phase image the cardiac phase image in the cardiac phase image sequence which has the best cardiac image matching metric of the second series of match metrics;

and/or wherein step e) further comprises:

e2) comparing the first breathing phase image to each cardiac phase image in the cardiac phase image sequence to derive a third series of match metrics; and e3) selecting as the first cardiac phase image the cardiac phase image in the cardiac phase image sequence which has the best cardiac image matching metric of the third series of match metrics.

According to this embodiment, the cardiac phase images may be synchronized with the intervention image and the breathing phase images using an image matching algorithm and therefore would not be reliant on ECG signals or other image matching algorithms discussed previously.

Figure 4:
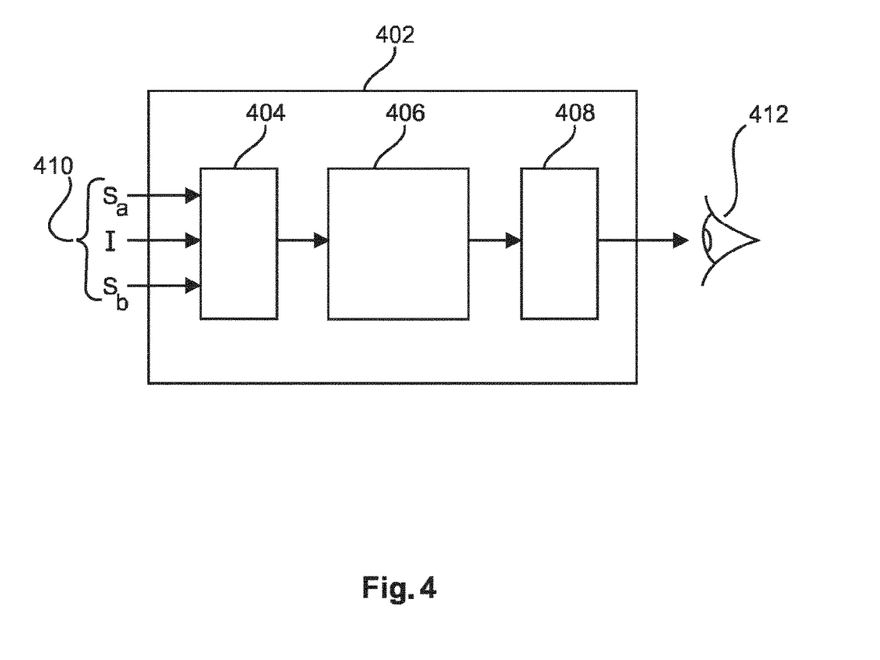
FIG. 4 shows a device according to an aspect of the invention.

According to an aspect of the invention, a device 402 for providing a digital subtraction algorithm is provided. The device comprises:

an interface unit 404;

processing unit 406;

and an output unit 408.

The interface unit is configured to provide (i) a cardiac phase image sequence comprising a plurality of cardiac phase images; (ii) a breathing phase image sequence comprising a plurality of breathing phase images; and (iii) an intervention image, wherein the intervention image is indexed with a first cardiac phase index.

The processing unit is configured to: select a first breathing phase image in the plurality of breathing phase images which is at a similar breathing phase to the intervention image, wherein the first breathing phase image is indexed with a second cardiac phase index; to generate a breathing corrected intervention image by subtracting the first breathing phase image from the intervention image; to select a first cardiac phase image corresponding to the second cardiac phase index; to select a second cardiac phase image corresponding to the first cardiac phase index; to generate a cardiac phase corrected image by subtracting the first cardiac phase image from the second cardiac phase image; to compensate the cardiac phase corrected image to account for breathing motions; and to subtract the motion compensated cardiac phase corrected image from the breathing corrected intervention image; and to provide an angiogram image.

The output unit 408 is configured to display the angiogram image to a user.

Therefore, the inputs 410 of the device 402 are the cardiac phase image sequence $S_a$, the intervention image I, and the breathing phase image sequence $S_b$.

According to an embodiment of the invention, the sequences are provided as a whole sequence, and the processing unit 406 parses the whole sequence natively to derive the cardiac phase image sequence $S_a$, the intervention image I, and the breathing phase image sequence $S_b$.

According to this aspect of the invention, the device is provided which enables relatively short cardiac motion and breathing motion sampling, so that a longer fluoroscopic examination (for example, a perfusion examination) may be performed without artefacts resulting from breathing motion appearing in the final image.

According to an embodiment of the invention, the device 402 is provided as previously discussed, wherein the interface unit 404 is further configured to provide external breathing phase information, wherein the breathing phase image sequence and the intervention image are synchronized to the external breathing phase information. The processing unit 406 is further configured to compare the external breathing phase information synchronized to the intervention image to the external breathing phase information synchronized to the images of the breathing phase image sequence, and to identify the first breathing phase image as the image in the breathing phase image sequence which is at a similar breathing phase to the intervention image.

According to an embodiment of the invention, the device 402 is provided wherein the processing unit 406 is further configured to compare the intervention image to each breathing phase image in the breathing phase image sequence, to derive a first series of match metrics, and select as the first breathing phase image the breathing phase image in the breathing phase image sequence which has the best match metric of the first series of match metrics.

According to an embodiment of the invention, the device 402 is provided wherein the interface device 404 is further configured to provide external cardiac phase information synchronized to the cardiac phase image sequence. The processing device 406 is further configured to select the first cardiac phase image corresponding to the second cardiac phase index using the external cardiac phase information, and/or to select the second cardiac phase image corresponding to the first cardiac phase index using the external cardiac phase information.

According to an embodiment of the invention, the device 402 is provided as described previously, wherein the processing unit 406 is further configured to compare the intervention image to each cardiac phase image in the cardiac phase image sequence, to derive a second series of match metrics, to select as the second cardiac phase image the cardiac phase image in the cardiac phase image sequence which has the best cardiac image matching metric of the second series of match metrics, and/or to compare the first breathing phase image to each cardiac phase image in the cardiac phase image sequence to derive a third series of match metrics, and to select as the first cardiac phase image the cardiac phase image in the cardiac phase image sequence which has the best cardiac image matching metric of the third series of match metrics.

According to an embodiment of the invention, the device 402 is provided wherein the interface unit 404 is further configured to provide an intervention image sequence containing a plurality of intervention images. The processing unit 406 is configured to process the successive intervention images in the intervention image sequence; and the output unit 408 is configured to display the angiogram as a sequence of successive angiogram images.

Advantageously, according to this embodiment, the X-ray image double-subtraction scheme discussed previously may be applied to a sequence of X-ray (angiogram) images. Therefore, a video of an angiographic examination, which does not contain breathing artefacts, can be provided. This allows the dynamics of a myocardial perfusion to be examined.

According to an embodiment of the invention, the device 402 is provided as discussed previously, wherein the processing unit 406 is configured to select any of the first breathing phase images, the first cardiac phase images, and the second cardiac phase images, with reference to the status of the breathing phase images, the first cardiac phase images, and the second cardiac phase images from a prior step.

Previously, it has been considered that each successive intervention image may be corrected independently of each other intervention image.

A reduction in complexity can be achieved if, between the processing of successive intervention images, the indexing of the breathing phase image sequence and the cardiac phase image sequence is retained.

According to this embodiment, when identifying a subsequent first breathing phase image, a subsequent first cardiac phase image, and a subsequent second cardiac phase image; the selection of these images, begins respectively, at the previous first cardiac phase index, second cardiac phase index, or the index of the previous first breathing phase image.

According to an embodiment, a linear programming method is applied to the images denoted by the previous first cardiac phase index, second cardiac phase index, or the index of the previous first breathing phase.

This is used to enable a beneficial selection of breathing status and/or cardiac status images which is more robust.

Advantageously, it is expected (for physiological reasons) that intervention images captured in a closely successive image of the sequence will, in practice, be closely correlated with prior breathing phase and cardiac phase images.

Therefore, using a priori knowledge of previous indexes leads to a reduction in complexity of the method, because it is more likely that the selection steps will identify the optimal image quickly if they begin searching the cardiac phase image sequence and the breathing phase image sequence from the last indexed position, rather than the beginnings of the sequences. This is an important concern, because the X-ray result is usually required in "real-time".

Figure 5:
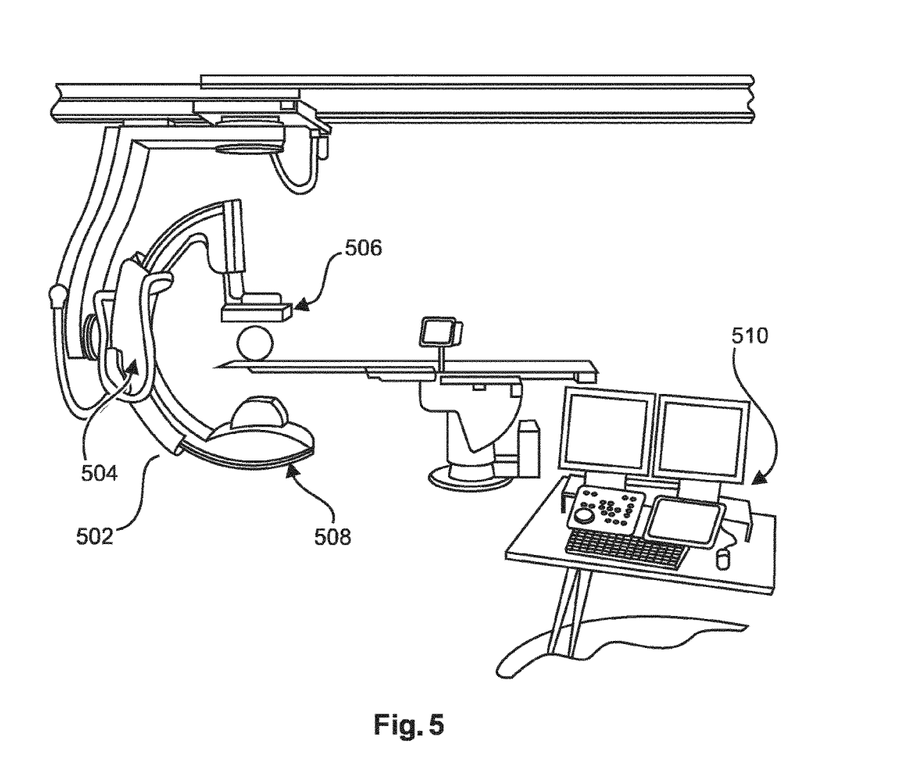
FIG. 5 shows an X-ray system according to an aspect of the invention.

According to a third aspect of the invention, there is provided an X-ray imaging arrangement 502.

The X-ray imaging arrangement comprises an X-ray acquisition device 504 with an X-ray source 506 and an X-ray detector 508. The arrangement also comprises a device 510 for providing a digital subtraction angiogram as previously described. The X-ray acquisition device is configured to acquire image data of the chest of a patient and to provide the data to the interface of the device for providing a digital subtraction angiogram.

According to a fourth aspect of the invention, a computer program element for controlling a device according to one of the previous descriptions is provided which, when the computer program element is executed by a processing unit, is adapted to perform the method steps as previously described.

According to a fifth aspect of the invention, a computer-readable medium having stored the program element discussed previously is provided.

A computer program element might therefore be stored on a computer unit, which might also be part of an embodiment of the present invention. This computing unit may be adapted to perform or induce performance of the steps of the method described above.

Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both the computer program that has the invention installed from the beginning, and a computer program that by means of an update turns an existing program into a program that uses the invention.

A computer program may be stored and/or distributed on a suitable medium, such as optical storage media or a solid state medium supplied together with, or as a part of other hardware, but may also be distributed in other forms, such as via the Internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to the device-type claims. However, a person skilled in the art will gather from the above, and the following description that, unless otherwise notified, in addition to any combination of features belonging to one type of subject-matter, also any other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A device for providing a digital subtraction angiogram, comprising:
    an interface unit;
    a processing unit;
    an output unit;
    wherein the interface unit is configured to provide (i) a cardiac phase image sequence ($S_a$) comprising a plurality of cardiac phase images, (ii) a breathing phase image sequence ($S_b$) comprising a plurality of breathing phase images, and (iii) an intervention image (I), wherein the intervention image is indexed with a first cardiac phase index;
    wherein the processing unit is configured:
    to select a first breathing phase image ($M_B$) in the plurality of breathing phase images which is at a similar breathing phase to the intervention image, wherein the first breathing phase image is indexed with a second cardiac phase index,
    to generate a breathing corrected intervention image ($D_1$) by subtracting the first breathing phase image from the intervention image,
    to select a first cardiac phase image corresponding to the second cardiac phase index, to select a second cardiac phase image corresponding to the first cardiac phase index,
    to generate a cardiac phase corrected image (D2) by subtracting the first cardiac phase image from the second cardiac phase image,
    to compensate the cardiac phase corrected image to account for breathing motions, and
    to subtract the motion compensated cardiac phase corrected image from the breathing corrected intervention image (D1) to provide an angiogram image (D); and
    wherein the output unit is configured to display the angiogram image to a user.

2. The device of claim 1, wherein the interface unit is further configured to:
    provide external breathing phase information, wherein the breathing phase image sequence and the intervention image (I) are synchronized to the external breathing phase information;
    wherein the processing unit is further configured to:
    compare the external breathing phase information synchronized to the intervention image to the external breathing phase information synchronized to the images of the breathing phase image sequence ($S_b$), and to identify the first breathing phase image as the image in the breathing phase image sequence which is at a similar breathing phase index to the first cardiac phase index.

3. The device of claim 1, wherein the processing unit is further configured to:
    compare the intervention image to each breathing phase image in the breathing phase image sequence ($S_b$) to derive a first series of match metrics, and to select as the first breathing phase image the breathing phase image in the breathing phase image sequence which has the best match metric of the first series of match metrics.

4. The device of claim 3, wherein the processing unit is further configured to:
    compare the intervention image to each cardiac phase image in the cardiac phase image sequence ($S_a$) to derive a second series of match metrics, to select as the second cardiac phase image the cardiac phase image in the cardiac phase image sequence which has the best cardiac image matching metric of the second series of match metrics, and/or to compare the first breathing phase image to each cardiac phase image in the cardiac phase image sequence, thereby deriving a third series of match metrics, and to select as the first cardiac phase image the cardiac phase image in the cardiac phase image sequence which has the best cardiac image matching metric of the third series of match metrics.

5. The device of claim 1, wherein the interface device is further configured to:
    provide external cardiac phase information synchronized to the cardiac phase image sequence;
    wherein the processing device is further configured to:
    select the first cardiac phase image corresponding to the second cardiac phase index using the external cardiac phase information, and/or to select the second cardiac phase image corresponding to the first cardiac phase index using the external cardiac phase information.

6. The device of claim 1, wherein the interface unit is further configured to:
    provide an intervention image sequence containing a plurality of intervention images;
    wherein the processing unit is configured to:
    process the successive intervention images in the intervention image sequence; and
    wherein the output unit is configured to:
    display the angiogram as a sequence of successive angiogram images.

7. The device of claim 6, wherein processing unit is configured to:
    select any of the first breathing phase image, the first cardiac phase image, and the second cardiac phase image with reference to a prior step.

8. An X-ray imaging arrangement, comprising:
    an X-ray acquisition device with an X-ray source and an X-ray detector; and
    a device for providing a digital subtraction angiogram according to claim 1;
    wherein the X-ray image acquisition device is configured to acquire image data of the chest of a patient, and to provide the data to the interface of the device for providing a digital subtraction angiogram.

9. A method for providing a digital subtraction angiogram, comprising the following steps:
    a) providing (i) a cardiac phase image sequence ($S_a$) comprising a plurality of cardiac phase images, (ii) a breathing phase image sequence ($S_b$) comprising a plurality of breathing phase images, and (iii) an intervention image, wherein the intervention image is indexed with a first cardiac phase index;

b) selecting a first breathing phase image (Mb) in the plurality of breathing phase images which is at a similar breathing phase to the intervention image, wherein the first breathing phase image is indexed with a second cardiac phase index;

c) generating a breathing corrected intervention image (D1) by subtracting the first breathing phase image from the intervention image;

d) selecting a first cardiac phase image corresponding to the second cardiac phase index;

e) selecting a second cardiac phase image corresponding to the first cardiac phase index;

f) generating a cardiac phase corrected image (D2) by subtracting the first cardiac phase image from the second cardiac phase image;

g) motion compensating the cardiac phase corrected image (D2) to account for breathing motions;

h) subtracting the motion compensated cardiac phase corrected image from the breathing corrected intervention image (I) to provide an angiogram image (D);

i) displaying the angiogram image.

10. The method of claim 9, wherein step a) further comprises:
  a1) providing external breathing phase information, wherein the breathing phase image sequence and the intervention image are synchronized to the external breathing phase information; and wherein step b) further comprises:
  b1) comparing the external breathing phase information synchronized to the intervention image to the external breathing phase information synchronized to the images of the breathing phase image sequence;
  b2) identifying the first breathing phase image as the image in the breathing phase image sequence which is at a similar breathing phase to the intervention image.

11. The method of claim 9, wherein step b) further comprises:
  b3) comparing the intervention image to each breathing phase image in the breathing phase image sequence to derive a first series of match metrics;
  b4) selecting as the first breathing phase image the breathing phase image in the breathing phase image sequence which has the best match metric of the first series of match metrics.

12. The method of claim 11, wherein step d) further comprises:
  d2) comparing the intervention image (I) to each cardiac phase image in the cardiac phase image sequence ($S_a$) to derive a second series of match metrics;
  d3) selecting as the second cardiac phase image the cardiac phase image in the cardiac phase image sequence which has the best cardiac image matching metric of the second series of match metrics, and/or wherein step e) further comprises:
  e2) comparing the first breathing phase image to each cardiac phase image in the cardiac phase image sequence to derive a third series of match metrics; and
  e3) selecting as the first cardiac phase image the cardiac phase image in the cardiac phase image sequence which has the best cardiac image matching metric of the third series of match metrics.

13. The method of claim 9, wherein step a) further comprises:
  a2) providing external cardiac phase information synchronized to the cardiac phase image sequence ($S_a$); wherein step c), further comprises:
  d1) selecting the first cardiac phase image corresponding to the second cardiac phase index using the external cardiac phase information, and/or wherein step e) further comprises:
  e1) selecting the second cardiac phase image corresponding to the first cardiac phase index using the external cardiac phase information.

14. A non-transitory computer-readable storage medium storing a computer program, which when executed by a processing unit, is adapted to perform the following steps:
  a) providing (i) a cardiac phase image sequence ($S_a$) comprising a plurality of cardiac phase images, (ii) a breathing phase image sequence ($S_b$) comprising a plurality of breathing phase images, and (iii) an intervention image, wherein the intervention image is indexed with a first cardiac phase index;
  b) selecting a first breathing phase image (Mb) in the plurality of breathing phase images which is at a similar breathing phase to the intervention image, wherein the first breathing phase image is indexed with a second cardiac phase index;
  c) generating a breathing corrected intervention image (D1) by subtracting the first breathing phase image from the intervention image;
  d) selecting a first cardiac phase image corresponding to the second cardiac phase index;
  e) selecting a second cardiac phase image corresponding to the first cardiac phase index;
  f) generating a cardiac phase corrected image (D2) by subtracting the first cardiac phase image from the second cardiac phase image;
  motion compensating the cardiac phase corrected image (D2) to account for breathing motions;
  h) subtracting the motion compensated cardiac phase corrected image from the breathing corrected intervention image (I) to provide an angiogram image (D);
  i) displaying the angiogram image.

* * * * *